United States Patent [19]

Labrie et al.

[11] Patent Number: 5,227,375
[45] Date of Patent: Jul. 13, 1993

[54] AROMATASE INHIBITORS

[75] Inventors: Fernand Labrie; Yves Merand, both of Quebec, Canada

[73] Assignee: Endorecherche, Inc., Canada

[21] Appl. No.: 477,024

[22] Filed: Feb. 8, 1990

[51] Int. Cl.$^5$ .................... C07J 1/00; C07J 13/00; A61K 31/565

[52] U.S. Cl. .................... 514/172; 514/177; 514/169; 552/638; 552/641; 552/642; 552/505; 540/114; 549/555

[58] Field of Search ............... 552/647, 638, 641, 642; 514/169, 177, 172; 540/114; 549/555

[56] References Cited

U.S. PATENT DOCUMENTS

| | | | |
|---|---|---|---|
| 3,318,925 | 5/1967 | Annof et al. | 552/647 |
| 3,380,886 | 4/1968 | Campbell et al. | 552/642 |
| 3,485,828 | 12/1969 | Zderic et al. | 552/510 |
| 3,591,607 | 7/1971 | Furst et al. | 552/638 |
| 3,766,213 | 10/1973 | Furst et al. | 562/499 |
| 3,952,018 | 4/1976 | Rosen | 514/177 |
| 4,596,796 | 6/1986 | Yamamoto et al. | 514/143 |
| 4,596,797 | 6/1986 | Schweikert et al. | 514/177 |
| 4,596,797 | 6/1986 | Schweikert et al. | 514/177 |
| 4,822,528 | 4/1989 | Colombo et al. | 514/177 |
| 4,824,830 | 4/1989 | Buzetti et al. | 514/177 |

FOREIGN PATENT DOCUMENTS

| | | | |
|---|---|---|---|
| 0115965 | 8/1984 | European Pat. Off. | 552/647 |
| 2558088 | 7/1977 | Fed. Rep. of Germany | 552/647 |
| 3612632 | 10/1987 | Fed. Rep. of Germany | 514/177 |

OTHER PUBLICATIONS

Brodie, A. M. H., et al., 1977, Endocrinology, 100, 1684–1685.
Covey, D. F., et al., 1981, J. Biol. Chem., 256: 1076–1079.
Covey, D. F. and Hood, W. F., 1981, Endocrinology, 108: 157–1599.
Brueggemeier and Katlic, 1987, Cancer. Res. 47: 4548–4551.
Henderson, 1987, J. Steroid Biochem. 27: 905–914.
Numazawa et al., 1987, J. Steroid Biochem. 28: 337–344.
Kruter et al., 1987, J. Steroid Biochem. 28: 139–145.
Snider, C. E. and Brueggemeier, R. W., 1985, J. Biol. Chem., 2626: 8685–8687.
Sherwin, P. F., et al., 1989, J. Med. Chem., 32, 651–658.
Giudici, D., et al., 1988, J. Steroid Biochem., 30.
Spinola, P. G., et al., 1988, Breast Cancer Res. Treat., 12, 287–296.
Brodie, A. M. H., 1987, J. Steroid Biochem., 27, 899–893.
Goss et al., Cancer Res. 46: 4823–4826.
Petrow, et al., 1983, J. Steroid Biochem. 19: 1491–1502.
Grunwell, et al., 1976, Steroids, 27, 759–771.
Solo, A. J., et al., 1982, Steroids, 40, 603–614.
Brueggemeier, R. W., et al., 1978, J. Med. Chem. 21, 1007–1011.
Snider, C. E., Brueggemeier, R. W. 1985, J. Biol. Chem. 262, 8685–8687.
Brueggemeier, R. W. and Li, P. K., 1988, Cancer Res. 48, 6808–6810.
J. H. Davies, et al., Proc. Am. Ass. Cancer Res. 30, abs 1204, 1989.
R. W. Brueggemeier, et al., Proc. Am. Ass. Cancer Res. 30, abs 1206, 1989.
R. De Coster, et al., Proc. Am. Ass. Cancer Res. 30, abs, 1207, 1989.

*Primary Examiner*—Robert T. Bond
*Assistant Examiner*—E. C. Ward
*Attorney, Agent, or Firm*—Ostrolenk, Faber, Gerb & Soffen

[57] ABSTRACT

Novel aromatase inhibitors are disclosed for use in therapeutic preparations for treatment of estrogen-dependent diseases. The compounds are specified 7α-substituted androstanedione and androstenedione derivatives which show a strong inhibitory activity towards aromatase. The invention includes synthesis and pharmaceutical compositions of said compounds.

35 Claims, No Drawings

OTHER PUBLICATIONS

Proceedings/Anneal meeting of the American Assoc. for cancer research, vol. 30, Mar. 1989, p. 303.

Schiavo, et al., "Tapetal changes in Beagle Dogs following Oral Administration of CGS 14796C, A Potential Aromatase Inhibitor", Fundamental and Applied Toxicology 10, 329-334 (1988).

CGS 16949A, a New Nonsteroidal Aromatase Inhibitor: Effects on Hormone-dependent and -independent Tumors in Vivo, Cancer Research 48, 834-838, Feb. 15, 1988.

Brodie, et al., "Aromatase in Breast Cancer and the Role of Aminoglutethimide and Other Aromatase Inhibitors", CRC, vol. 5, Issue 4, pp. 361-396, 1986.

Coombes, et al., "4-Hydroxyandrostenedione in Treatment of Postmenopausal Patients with Advanced Breast Cancer", The Lancet, Dec. 1, 1984, pp. 1237-1239.

Brooks, et al., "A-Ring Substituted Estrogens as Inhibitors of the MXT Transplantable Mammary Ductal Carcinoma", Cancer Research 47 Sep. 1, 1987, pp. 4623-4629.

Brodie, et al., "Inhibition of Estrogen Biosynthesis and Regression of Mammary Tumors by Aromatase Inhibitors", pp. 179-190.

C. T. Walsh, "Suicide Substrates, Mechanism-based Enzyme Inactivators: Recent Developments", Ann. Rev. Biochem., 1984, 53: 493-535.

Vanden Broek et al. Ger Offen, 2417846 Oct. 24, 1974 Chemical Abstracts vol. 82, 1975, Abstract 43655c.

Akzo Israeli 45022 Sep. 29, 1978 Chemical Abstracts vol. 93, 1980 Abstract 8388y.

Agarwal et al Endocinology, 1988 123(5) 2187-93 Chemical Abstracts vol. 110, 1989, Abstract 88835z.

Chan J. Steroid Biochem, 1979 11(3) 1193-6 Chemical Abstracts vol. 92, 1980 Abstract 158066.

Chemical Abstracts vol. 85, 1976, Abstract 124277d.

AROMATASE INHIBITORS

BACKGROUND OF THE INVENTION

This invention relates to novel steroidal aromatase inhibitors. More particularly, certain preferred embodiments of the invention relate to 7α-substituted androstenedione and androstanedione analogs which inhibit this enzyme.

BRIEF DESCRIPTION OF THE PRIOR ART

During the treatment of certain estrogen-dependent diseases, it is important to greatly reduce or, if possible, eliminate estrogen-induced effects. Alternative or concurrent therapy to administration of antiestrogens could involve attempts to block the production of estrogen such that none is available to activate receptor sites. The blockade of aromatase, an enzyme that synthesis estrogens from androgens (e.g. estradiol from testosterone) has been intensively studied in view of developing pharmaceutical drugs useful in the therapy of estrogen-dependent diseases, particularly breast cancer (Walsh, C., 1984, Ann. Rev. Biochem., 53, 493–535; Brodie, A. M. H. et al., 1977, Endocrinology, 100, 1684–1685; Convey D. F. et al, 1981, J. Biol. Chem., 256: 1076–1079; Covey D. F. and Hood, W. F., 1981, Endocrinology, 108: 157–1599; Brueggemeier and Katlic, 1987, Cancer. Res. 47: 4548–4551; Henderson, 1987. J. Steroid Biochem. 27: 905–914; Numazawa et al., 1987. J. Steroid Biochem. 28: 337–344; Kruter et al., 1987, J. Steroid Biochem. 28: 139–145; Snider, C. E. and Brueggemeier, R. W., 1985, J. Biol. Chem., 262: 8685–8687; Sherwin, P. F. et al., 1989, J. Med. Chem., 32, 651–658; Giudici, D. et al., 1988, J. Steroid Biochem., 30, these drugs have shown an "in vivo" inhibitory effect on the growth of mammary tumors (Spinola, P. G. et al., 1988, Breast Cancer Res. Treat., 12, 287–296; Brodie, A. M. H. et al., 1982, Adv. Exp. Med. Biol., 138, 179–196; Brooks, S. C. et al., 1987, Cancer Research, 47, 4623–4629; Schieweck, K., 1988, Cancer Research, 48, 834–838); Schiavo et al., 1988, Fund, Appl. Toxicol, 10, 329–334) but few of these have been used in women for the therapy of breast cancer. Examples of those which have been used are 4-hydroxy-4androstenedione and aminoglutethimide (Coombes, R. C. et al., 1984, The Lancet, 1237–1239; Brodie, A. M. H. 1987, J. Steroid Biochem., 27, 899–893; Goss et al., Cancer Res. 46: 4823–4826; Brodie, A. M. H. and Santen, R. J., 1986, in Davies, S., CRC critical reviews in oncology/hematology, vol. 5, Boca Raton: CRC Press: 361).

Schweikert et al., 1986, U.S. Pat. No. 4,596,796, disclose the use of aromatase inhibitors for prophylaxis and/or treatment of benign prostatic hyperplasia.

U.S. Pat. No. 4,822,528 discloses 4-substituted 6-alkylidenandrostene-3,17-dione derivatives as aromatase inhibitors.

U.S. Pat. No. 4,824,830 disclosed 6- or 7- methyl-androsta-1,4-diene-3,17-diones as aromatase inhibitors..

U.S. Pat. No. 3,766,213 discloses the synthesis of retrosteroids and more particularly a method for the formation of the A-ring of retrosteroids.

Derivatives of 6-methylene-4-androstene-3-ones are described by Petrow et al., 1983 (J. Steroid Biochem. 19: 1491–1502).

Grunwell et al., 1976, Steroids, 27, 759–771 and Solo, A. J. et al., 1982, Steroids, 40, 603–614 discloses the synthesis of a series of 7α-alkyltestosterone derivatives and describe their biological activities.

Brueggemeier, R. W. et al., 1978, J. Med. Chem. 21, 1007–1011 and Snider, C. E., Brueggemeier, R. W., 1985, J. Biol. Chem., 262, 8685–8687 disclose the synthesis and aromatase inhibitory activity of 7α-(4'-amino)phenylthio-androstenedione derivatives.

Brueggemeier, R. W. and Li, P. K., 1988, Cancer Research 48, 6808–6810, disclose that 7α-(4'-amino)phenylthio-4-androstene-3,17-dione inhibits the growth of DMBA-induced mammary carcinoma in rats.

J. H. Davies et al., Proc. Am. Ass. Cancer Res. 30, abs 1204, 1989, disclose the use of 4-hydroxy-androstenedione in human.

K. Schieweck et al., Proc. Am. Ass. Cancer Res. 30, abs 1205, 1989, disclose the use of CGS 16949A an anti-tumor agent.

R. W. Brueggemeier et al., Proc. Am. Ass. Cancer Res. 30, abs 1206, 1989, disclose the synthesis and activity of 7-alkyl and -aryl substituted derivatives of 4,6-androstadiene -3, 17-diones and 1,4,6-androstatriene -3,17diones.

R. De Coster et al., Proc. Am. Ass. Cancer Res. 30, abs. 1207, 1989, discloses the use of novel triazole derivatives R76713 as aromatase inhibitor.

U. Nickisch and H. Laurent in German patent D.E. 3612632, A₁, 1987 disclose the synthesis of 7α-propyl-steroids.

J. A. Zderic in U.S. Pat. No. 3,485,828, 1969, disclose the synthesis of 6,7-ethylene and 6,7-substituted ethylene steroid derivatives.

New aromatase inhibitors capable of effectually blocking the activity of aromatase while minimizing side effects and maximizing in vivo stability are desirable in the art for possible use in treating estrogen-sensitive diseases.

OBJECTS OF THE INVENTION

It is an object of the present invention to provide a steroidal inhibitor of aromatase for therapeutic use, and pharmaceutical compositions thereof.

It is another object of the invention to provide methods of inhibiting aromatase using pharmaceutical compositions with good in vivo stability and/or low tendency to induce undesirable side effects.

SUMMARY OF THE INVENTION

The above and other objects are accomplished by providing aromatase-inhibiting compounds, and pharmaceutical compositions comprising therapeutically effective amounts of at least one of said compounds, wherein the aromatase inhibiting compounds have the following molecular structure.

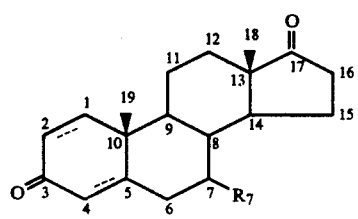

Wherein the structure is either unsubstituted or hydrogen substituted at the 4- and 6- positions, and wherein the dotted lines represent optional double bonds (4-androstene species being preferred); wherein $R_7$ is selected from the group consisting of alkenyl, alkynyl, alkyl, epoxyalkyl, cyclopropyl alkyl and their halogen-substituted derivatives.

All aromatase-inhibiting compounds herein have an androstenedione nucleus, the atom numbers and ring letters of which are as set forth above. The following conventions apply to structural formulae set forth herein. Unless specifically designated to the contrary, substituents may have either α or β stereochemistry or, where valence permits may represent one substituent in α position and another in β position, Presence of optional double bonds are independent of each other. All structures includes salts thereof.

Atoms of any androstenedione nucleus for which no substituent is shown or described may optionally be substituted or unsubstituted. Those atoms having a defined substituent may optionally be further substituted by other substituents where their valence permits such further substitution. As used herein, the term "lower", when describing a chemical moiety means a moiety having 8 or fewer atoms. For instance, a "lower alkyl" means a $C_1$ to $C_6$ alkyl. Any moiety of more than two atoms may be straight- or branched-chain unless otherwise specified.

A substitution at the 16 position is preferred in order to avoid the reduction of the 17-keto group which could cause the compounds to possess androgenic activity and potentially increase undesirable side effects in women.

$R_1$ is preferably a substituent of fewer than 8 atoms, or even a shorter ($C_1$-$C_4$) alkenyl, ($C_1$-$C_4$) alkynyl, or $C_1$-$C_4$ alkyl or ($C_1$-$C_4$) epoxyalkyl, cyclopropyl alkyl or halogeno-substituted derivatives thereof. In certain embodiments, $R_1$ is in the alpha position and $CH_2Y$ wherein Y is selected from the group consisting of —CH=$CH_2$, —C≡CH, —CH=$CCH_3$, —C≡$CH_3$,

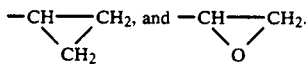

In Some embodiments, there are a plurality of points of unsaturation in the $C_7$ substituent.

The aromatase inhibition is preferably a 4androstenedione substituted as taught herein. Other embodiments include but are not limited to 5α-androstanedione and 5α-androstanedione. The aromatase inhibitors of the invention is used to treat estrogen-sensitive diseases by, for example, inhibiting the production of estrogen. These diseases include, but are not limited to breast cancer, ovarian cancer, endometriosis, benign breast disease, gynecomastia, uterine fibroma, precocious puberty and benign prostatic hyperplasia. The pharmaceutical compositions may also be useful in the control of fertility in women and infertility in men.

Aromatase-inhibiting compounds of the invention may also inhibit the activity of other estrogen-producing enzymes, especially, but not limited to 17β-hydroxysteroid dehydrogenase and estrogen sulfatase.

In one alternative embodiment, the 16 carbon in the D ring is replaced with heteroatom capable of inhibiting reduction of 17-keto.

DETAILED DESCRIPTION OF CERTAIN PREFERRED EMBODIMENTS

In certain preferred embodiments of the invention, therapeutic compositions may comprise one or more compounds represented by the formula II:

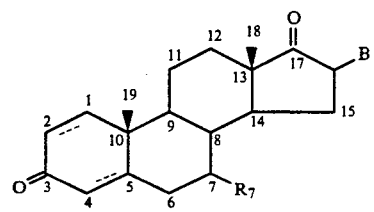

Wherein $R_7$ is selected from the group consisting of alkylene, alkylnylene, cyclopropyl alkyl, epoxyalkyl and their halogeno-substituted derivatives and wherein B is a stabilizing substituent which inhibits reduction of the 17-keto group. B is preferably a poor leaving group and is preferably even capable of steric hindrance of 17-keto reduction, (either by decreasing the aromatase-inhibiting compounds affinity for 17β-hydroxysteroid dehydrogenase, or otherwise). In preferred embodiments, B is selected from the group consisting of: methyl, ethyl, iso-propyl, t-butyl, phenyl, tolyl and triphenylmethyl.

Alternatively, reduction of 17-keto may be inhibited by placing an appropriate heteroatom in the 16 position of the D ring.

By way of example, some preferred aromatase inhibitors in accordance with the invention include but are not limited to are:

7α-allyl-4-androsten-3,17-dione

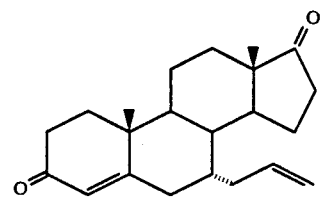

7β-allyl-5β-androstan-3,17-dione

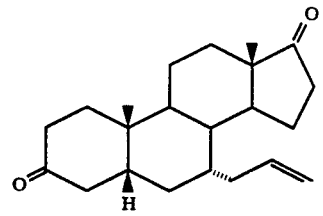

7α-allyl-5α-androstan-3,17-dione

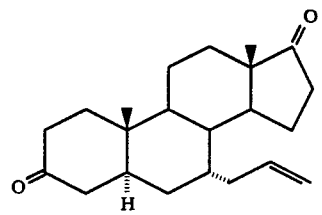

7α-allyl-16-oxo-4-androstan-3,17-dione

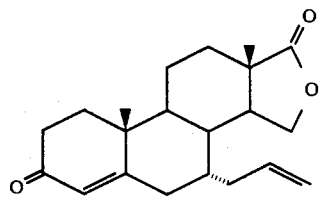

7α-allyl-16-oxo-5β-3,17-dione

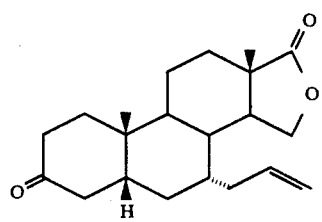

7α-allyl-16-oxo-5α-androstan-3,17-dione

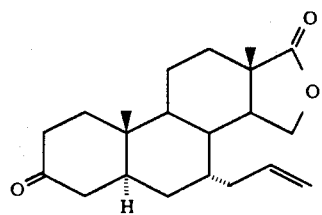

7α-(2-propynyl)-4-androsten-3,17-dione

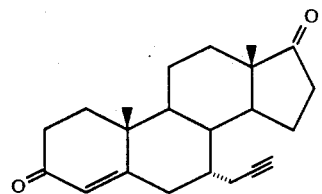

7α-(2-propynyl)-5α-androstan-3,17-dione

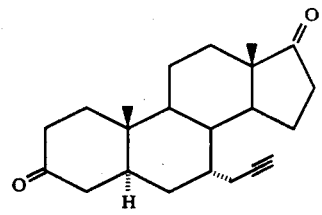

7α-(2-propynyl)-16-oxo-4-androstan-3,17-dione

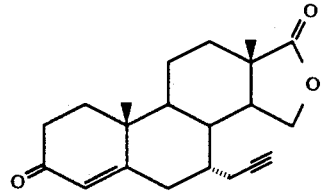

When aromatase inhibitors in accordance with the invention are used in the treatment of estrogen-related diseases, they are preferably administered at a dosage from about 5 mg to about 2000 mg of active expedient (i.e. aromatase inhibitor), per day per 50 kg of body weight, most preferably from about 1.0 mg to about 20 mg per day per kg of body weight.

The aromatase inhibitors are preferably prepared as pharmaceutical compositions together with pharmaceutically acceptable carriers and diluents. When prepared for parenteral injection, an inhibitor of aromatase activity may be prepared in a carrier preferably selected from the group consisting of saline, water, aqueous ethanol and oil.

When a pharmaceutical composition of the invention is prepared for oral ingestion, the composition preferably includes at least one inhibitor of aromatase activity wherein the total concentration of all such inhibitors in said pharmaceutical composition is from about 1% to about 95% of the composition (by weight), and preferably from about 5% to about 20%. The composition preferably further includes a pharmaceutically acceptable diluent, for example, starch or lactose with or without tartrazine. Slow release pharmaceutical products comprising the novel inhibitors of aromatase activity may be incorporated into slow release pharmaceutical products which, other than addition of the novel inhibitors, may be prepared by known methods and administered orally as well as parenterally.

In certain alternative embodiments, the pharmaceutical composition of the invention may be formulated for sustained release in accordance with known techniques. These sustained release formulations are preferably prepared in an appropriate manner for either oral, intramuscular, or subcutaneous administration.

Set forth below is a detailed description of preferred synthetic techniques for producing certain preferred aromatase inhibitors in accordance with the invention.

EXAMPLES OF SYNTHESIS OF PREFERRED AROMATASE INHIBITORS (SEE SCHEMA I AND SCHEMA II)

Instrumentation

The IR spectra were taken on a Perkin-Elmer 1310 spectrophotometer. Proton NMR spectra were recorded on a Varian EM-360A (60 MHz) or a Varian XL-200 (MHz) instrument. The following abbreviations have been used: s, singlet; d, doublet; dd, doublet of doublet; t, triplet; q, quadruplet; and m, multiplet. Chemical shifts are reported in δ values relative to tetramethylsilane (TMS) or chloroform as internal standard.

For flash chromatography, Merck-Kiesel gel 60(230–400 mesh A.S.T.M) was used. All solvents used for chromatography have been distilled. Unless otherwise indicated, starting material and reagents were obtained commercially and were used as such or purified by standard means.

7α-allyl-17β-hydroxy-4-androsten-3-one, "EM 172".

To a solution of 17β-acetoxy-4,6-androstadien-3-one 1 (2.0 g, 6.1 mmol) in dry dichloromethane (130 ml) was added titanium tetrachloride (5.36 g, 3.1 ml, 28 mmol) at −70° C. The reaction mixture was allowed to stir for 5 min. Then, a solution of allyltrimethylsilane (4.0 g, 5.6 ml, 35 mmol) in dry dichloromethane (10 ml) was added over a period of 10 min and the resulting solution stirred during 1 hour at −70° C. followed by 1 hour at −20° C. Afterwards, the solution was diluted with 150 ml of ether and was washed with water (6×100 ml), dried, filtrated and concentrated to yield the crude 17β- acetoxy-7α-allyl-4-androsten-3-one which was immediately hydrolyzed.

To a solution of crude acetate in methanol (100 ml) was added aqueous hydrochloric acid (10 ml, 5N). The reaction mixture was heated at reflux for 1 hour. Then, most of the methanol was evaporated and the residue was transferred into a separatory funnel with a mixture of ether: dichloromethane (100 ml, 1:1) and water (50 ml) and was then washed thoroughly with water. The organic phase was dried, filtered and concentrated to a solid. The crude material was purified by flash chromatography (hexane: acetone, 9:1 and 4:1) to yield 630 mg, 32% of compound EM 172. m.p. 208°-210° C., IR (KBr) $\nu_{max}$ cm$^{-1}$: 3550-3250 (OH), 1645 (C=O), 1610 (C=C); $^1$H-NMR (δppm): 5.72 (1H,s,—CH=C—), 5.65 (1H,m,—CH=CH$_2$), 5.00 (2H,m,—CH=CH$_2$), 3.67 (1H,t,J=8.5 Hz,—CHOH), 1.22 (3H, S,—$_{19}$CH$_3$), 0.81 (3H,s,—$_{16}$CH$_3$).

7α-allyl-4-androsten-3,17-dione, "EM 173"

A mixture of EM 172 (100 mg, 0.3 mmol), pyridinium chlorochromate (100 mg, 0.46 mmol), sodium acetate (75 mg, 0.91 mmol) and 4 Å molecular sieve (200 mg) in dry dichloromethane (5 ml) was stirred at 25° C. for 2 hours. The, the reaction mixture was filtered through a silica gel pad with ether as eluent and the filtrate was evaporated to a solid. The residue was recrystalized form dichloromethane and ether to give 81 mg, 81% of the desired diketone EM 173. m.p. 219°-221° C., IR (KBr) $\nu_{max}$ cm$^{-1}$: 1720 (C=O, ketone), 1670 (C=O, enone), 1635 (C=C), 1607 (C=C); $^1$H-NMR (δppm): 5.74 (1H,s,—CH=C—), 5.68 (1H,m.—CH=CH$_2$), 5.03 (2H, m,—CH=CH$_2$), 1.23 (3H, s, —$_{19}$CH$_3$), 0.93 (3H, s,—$_{18}$CH$_3$).

7α-allyl-5β-androstan-3,17-dione, "EM 176" and 7α-allyl-17β-hydroxy-5β-androstan-3-one, "EM 178".

To a stirred suspension of copper iodide (57 mg, 0.3 mmol) in dry tetrahydrofuran (5 ml) cooled to 0° C. was added methyllithium (215 μl of a 1.4M solution in ether, 0.3 mmol). The reaction mixture was cooled to −50° C. and then 2 ml hexamethylphosphoramide and diisobutylaluminum hybride (4 ml of a 1M solution in hexane, 4 mmol) were added successively. The mixture was stirred for 30 min. at −50° C. and EM 173 (50 mg, 0.15 mmol) in 2 ml of tetrahydrofuran was added. After being stirred at −50° C. for 2 hours, the solution was diluted with 30 ml of ether and was washed with aqueous hydrochloric acid (2×5 ml, 10% aqueous) and water (6×15 ml). The etheral phase was dried, filtered and concentrated to an oil. The residue was purified by column chromatography (hexane:acetone, 9:1) to give EM 176, 11 mg, 22%; EM 173, 8.5 mg, 17%; EM 178, 2.5 mg, 5% and EM 172, 13.5 mg, 26% obtained in that order from the column. N.B. EM 176: IR (neat) $\nu_{max}$cm$^{-1}$: 1730 (C=O), 1710 (C=O), 1632 (C=C); $^1$H-NMR (δppm): 5.74 (1H,m,—CH$_2$), 5.04 (2H, m, —CH=CH$_2$), 2.68 (1H, d of d, J=13.20 Hz and J=15.55 Hz, O=C—CH$_{ax}$H$_{eq}$CH—, 1.11 (3H,s,—$_{19}$CH$_3$), 0.90 (3H, s,—$_{16}$CH$_e$). EM 178: IR (neat $\nu_{max}$ cm$^{-1}$: 3600-3140 (OH), 1708 (C=O), 1635 (C=C); $^1$H-NMR (δppm): 5.72 (1H,m,—CH=CH$_2$), 5.03 (2H,m,—CH=CH$_2$), 3.68 (1H,t, J=8.40 Hz, —CHOH), 2.70 (1H, dd, J=13.55 Hz and J=15.55 Hz, O=C—CH$_{ax}$H$_{eq}$CH—), 1.10 (3H,s,—$_{19}$CH$_3$), 0.79 (3H,s,—$_{16}$CH$_3$).

17α-allyl-17β-(t-butyldimethylsilyloxy)-4-androsten-3-one, "2"

To a solution of EM 172 (420 mg, 1.28 mmol) in a mixture of dry tetrahydrofuran and dimethylformamide (14 ml, 1:1) cooled at 0° C. was added imidazole (700 mg, 10.2 mmol) and t-butyldimethylsily chloride (770 mg, 5.1 mmol). The reaction mixture was allowed to warm up to 25° C. and was stirred during 20 hours. Then, the mixture was diluted with 150 ml of ether and was washed thoroughly with water. The ethereal phase was dried, filtrated and concentrated to an oil which was purified by flash chromatography (hexane:acetone, 9:1) to yield 546 mg, 96% of silylether 2. IR (neat) $\nu_{max}$ cm$^{-1}$: 1670 (C=O), 1632 (C=C), 1610 (C=C); $^1$H-NMR (δppm): 5.70 (1H,s,—CH=C—), 5.67 (1H,m,—CH=CH$_2$), 4.99 (2H,m,—CH=CH$_2$), 3.56 (1H,t,J=8.5 Hz,—CHOSi—), 1.19 (3H,s,—$_{19}$CH$_3$), 0.87 (9H,s,—C(CH$_3$)$_3$), 0.75 (3H,s—$_{18}$CH$_3$), 0.00 (6H,s,—Si(CH$_3$)$_2$).

17β-hydroxy-7α-propyl-5α-androstan-3-one, "EM 185"

A large excess of lithium wire (405 mg, 58 mmol) cut into short sections was added to 12 ml of freshly distilled ethylenediamine cooled in a water bath to 15° C. The mixture was stirred until dark blue (5 min.). Then, a solution of enone 2 (150 mg, 0.34 mmol) and t-butyl alcohol (435 μl), in 2.5 ml of dioxane was added dropwise rapidly; additional dixoane was used to complete the transfer. The reaction mixture was stirred for 45 min. while being maintained below room temperature by addition of ice to the water bath. Afterwards, ammonium chloride (1.25 g) and water (40 ml) were added successively to quench the reaction. The resulting mixture was extracted with ether (3×30 ml). The etheral phase was washed thoroughly with water, dried, filtered and concentrated to an oil which was directly hydrolyzed.

To a solution of crude silyl ether in methanol (5 ml) was added aqueous hydrochloric acid (2 ml, 10% aqueous). The solution was heated at reflux for 1 hour. Then, the reaction mixture transferred into a separatory funnel with ether (50 ml) and water (20 ml) was washed with water (6×20 ml). The organic phase was dried, filtrated and concentrated to a solid. The crude material was purified by flash chromatography (hexane:acetone, 9:1) to yield 38.5 mg, 34% of EM 185. m.p. 154°-156° C., IR (KBr) $\nu_{max}$ cm$^{-1}$: 3560-3100 (OH), 1700 (C=O); $^1$H-NMR (δppm): 3.65 (1H,t,J=8.1 Hz, —CHOH), 1.04 (3H,s,—$_{19}$CH$_3$), 0.88 (3H,t,J=6.7 Hz, —CH$_2$CH$_3$), 0.76 (3H,s,—$_{18}$CH$_3$).

7α-allyl-17β-hydroxy-5α-androstan-3-one, "EM 197"

A solution of EM 172 (500 mg, 1.52 mmol) and t-butyl alcohol (5 ml) in dioxane (25 ml) was added dropwise with stirring to a solution of lithium (68 mg, 9.7 mmol) in liquid ammonia (100 ml) over a period of 2 minutes. The reaction mixture was allowed to stir for another 5 minutes. The lithium amide formed was neutralized by the addition of ammonium chloride (2 g) and the ammonia was allowed to evaporate. The residue was dissolved in ether (200 ml), washed with water (6×50 ml), dried, filtrated and concentrated to an oil. The residue was purified by flash chromatography (hexane:acetone, 4:1) to yield 254 mg, 50.5% of hydroxyketone EM 197: m.p. 170°-172° C., IR (KBr) $\nu_{max}$ cm$^{-1}$: 3560-3300 (OH), 1695 (C=O), 1633 (C=C); 1H-NMR (δppm): 5.66 (1H,m,—CH—CH$_2$), 4.96 (2H,m,'CH=CH$_2$), 3.65 (1H,t,J=8.30 Hz,—CHOH), 1.04 (3H,s,—$_{19}$CH$_3$), 0.77 (3H,s—$_{18}$CH$_3$).

7α-allyl-5α-androstan-3,17-dione, "EM 198"

The preparation of this diketone (EM 198) was performed as described for diketone EM 173 (vide supra) with the following quantities; EM 197 (56 mg, 0.168 mmol), pyridinium chlorochromate (110 mg, 0.5 mmol), sodium acetate (83 mg, 1 mmol) and 4 Å molecular sieve (110 mg), dichloromethane (5 ml), 0° C.→25° C., 4 hours. The residue was purified by flash chromatography (hexane:acetone, 9:1) to give 39 mg, 71% of diketone EM 198. IR (neat) $\nu_{max}$ cm$^{-1}$: 1732 (C=O), 1709 (C=O), 1635 (C=C); $^1$H-NMR (δppm): 5.69 (1H,m,—CH=CH$_2$), 5.00 (2H,m,—CH=C$\underline{H}_2$), 1.06 (3H,s,—$_{19}$C$\underline{H}_3$), 0.89 (3H,s,—$_{18}$C$\underline{H}_3$).

7α-allyl-3,3-ethylenedioxy-17β-hydroxy-5-androstane

A mixture of EM 197 (620 mg, 1.87 mmol), ethylene glycol (200 mg, 180 μl, 3.22 mmol) and p-toluenesulfonic (10 mg, 0.058 mmol) dissolved in 80 ml of dry benzene was refluxed (Dean-Stark) for 2 h 45 min. under nitrogen. Then, ether (100 ml) was added and the resulting solution washed successively with sodium carbonate (2×30 ml, 5% aqueous) and with water (4×30 ml). The organic phase was dried, filtered and concentrated to a solid. The residue was purified by filtration on silica with hexane:acetone (4:1) and dichloromethane to give 550 mg, 78% of dioxolane, IR (KBr) $\nu_{max}$ cm$^{-1}$: 3600-3100 (OH), 1100-1080 (C—O); $^1$H-NMR (δ ppm): 5.69 (1H,m,—CH=CH$_2$), 5.00 (2H,m,—CH=C$\underline{H}_2$), 3.92 (4H,s,—OC$\underline{H}_2$CH$_2$O—), 3.64 (1H,t,J=8.20 Hz,—C$\underline{H}$OH), 0.84 (3H,s,—$_{19}$C$\underline{H}_3$), 073 (3H,s,—$_{18}$C$\underline{H}_3$); MS m/e (70 eV): 374 (M+).

17β-hydroxy-7α-(2,3'-epoxypropyl)-5α-androstan-3-one ("EM 206")

A mixture of above olefin (380 mg, 1.02 mmol), m-chloroperbenzoicacid (1.2 g, 50-60%, 3.47 mmol) and sodium acetate (3.8 g) in dry dichloromethane (30 ml) was stirred for 24 h at 25° C. Then, ether (100 ml) was added and the resulting solution was washed successively with a solution of sodium carbonate (3×, 50 ml) and with water (3×50 ml). The organic phase was dried, filtrated and concentrated to a solid. The residue was purified by flash chromatography (hexane:acetone, 4:1) to give 115 mg, 29% of the epoxide as a solid. IR (KBr) $\theta_{max}$cm$^{-1}$: 3550-3100 (OH), 1100-1080 (C—O); $^1$H-NMR (s ppm): 3.93 (4H,s,—OCH$_2$—CH$_2$—O—), 3.62 (1H, t, J=8.25 Hz,—C$\underline{H}$OH), 2.90 (1H, massive, —C$\underline{H}$OH$_2$—), 2.77 (1H, dt apparent, J=16.2 Hz and J=4.7 Hz, CHOC$\underline{H}$H) 2.48 (1H, m, CHOCH$\underline{H}$), 0.86 (3H,s,—$_{19}$C$\underline{H}_3$), 0.74 (3H,s,—$_{18}$C$\underline{H}_3$); MS m/e (70 ev): 390 (M+).

This compound was hydrolyzed with p-toluenesulfonic acid in acetone and the 17β-hydroxy group oxidized with Jone's reagent into the (2',3'-epoxypropyl)-5α-androstan-3,17-dione ("EM 206").

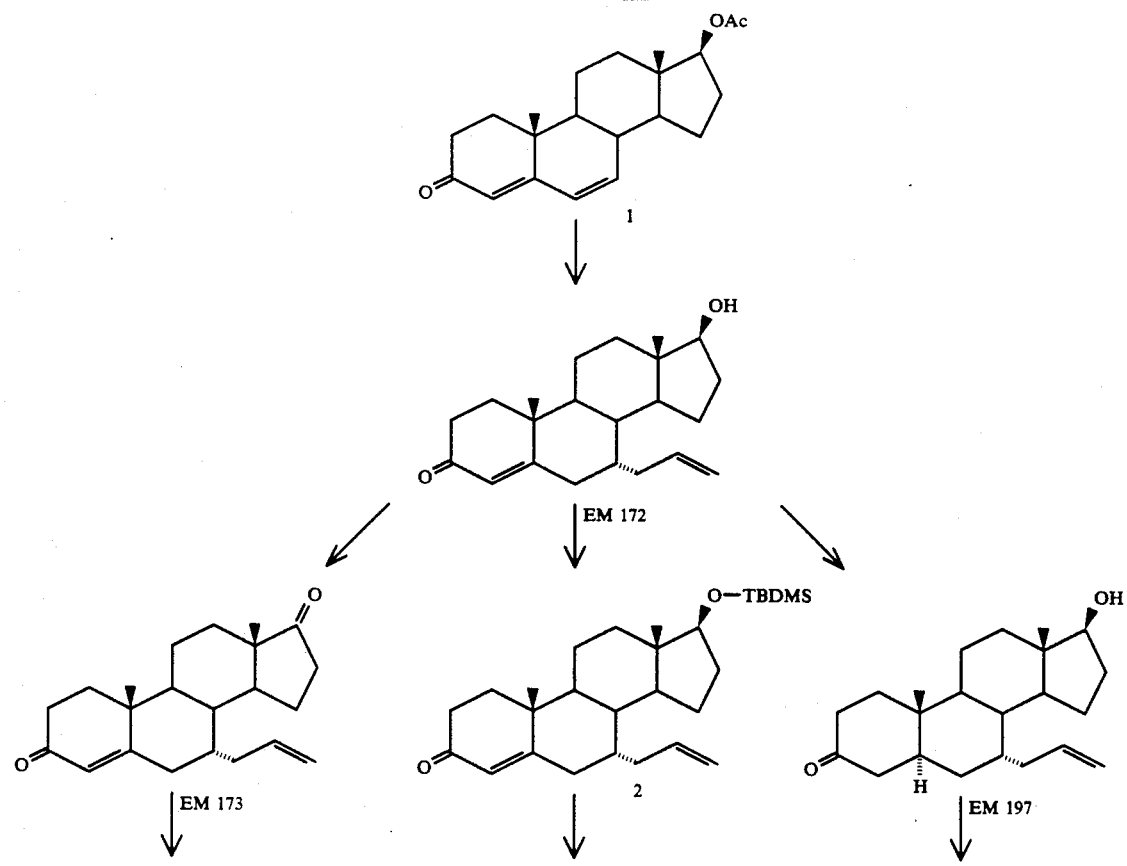

SCHEME I

-continued
SCHEME I
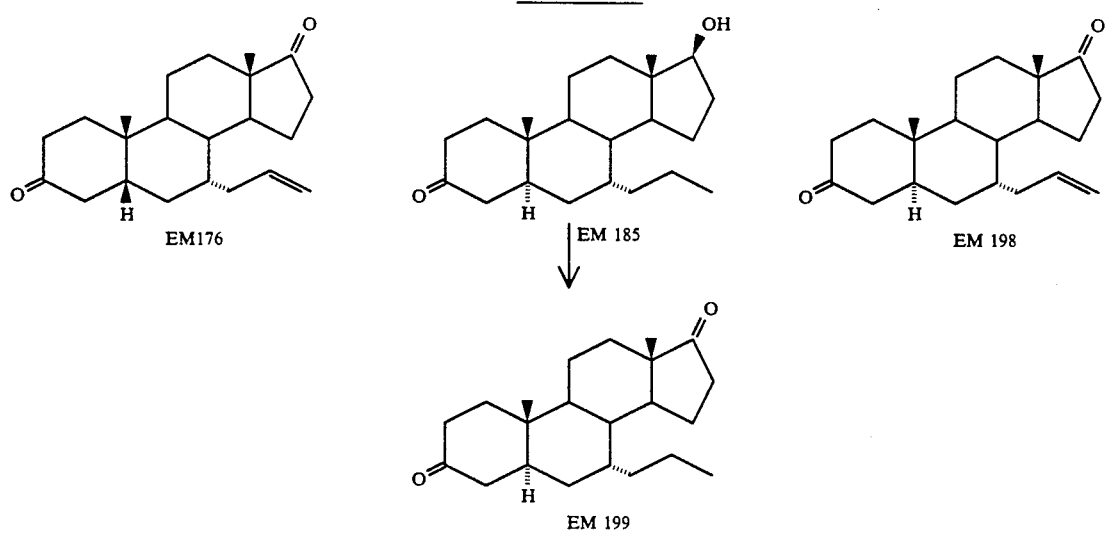
SCHEME II
7α-allyl-16-oxo-4androstan-3,17-dione ("EM 230")
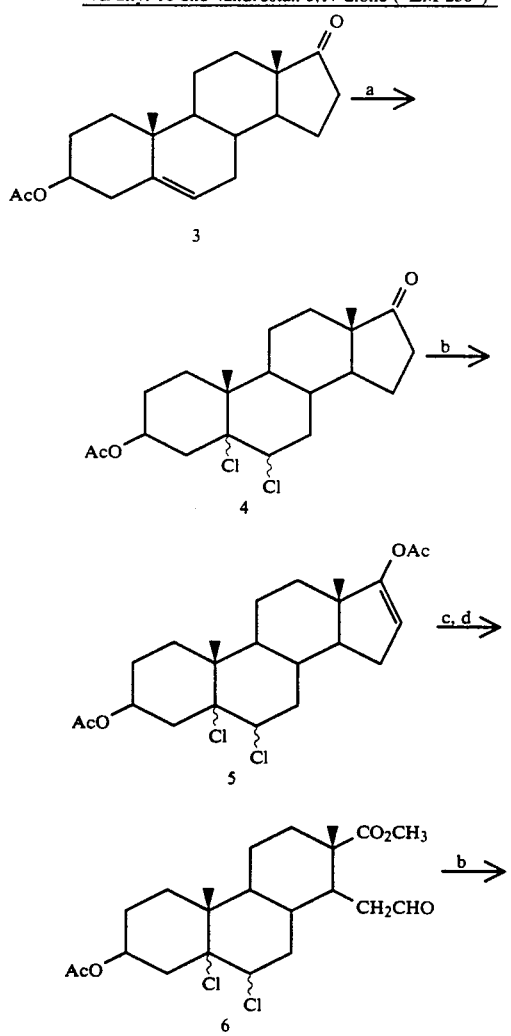
-continued
SCHEME II
7α-allyl-16-oxo-4androstan-3,17-dione ("EM 230")
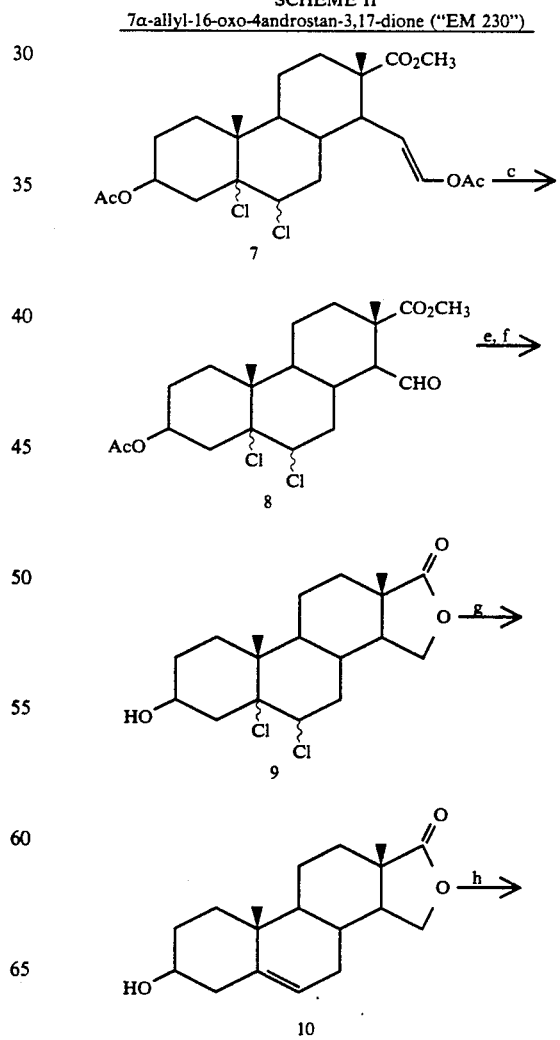

-continued
SCHEME II
7α-allyl-16-oxo-4androstan-3,17-dione ("EM 230")

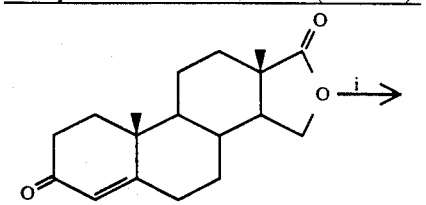

11

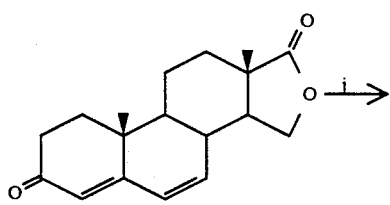

12

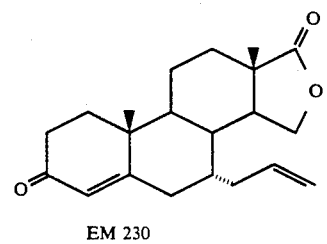

EM 230 a) SOCl$_2$, pyridine;
b) CH$_2$=C(OAc)CH$_3$, p-TsOH, Δ;
c) 1) O$_3$, CH$_2$Cl$_2$, AcOH, −70° C., 2) (CH$_3$)$_2$S;
d) CH$_2$N$_2$, Et$_2$O;
e) NaBH$_4$, EtOH;
f) Na$_2$CO$_3$;
g) Zn, AcOH;
h) Jone's reagent;
i) dichlorodicyanobenzoquinone, H$^+$, Dioxane;
j) TiCl$_4$, allyltrimethylsilane, CH$_2$Cl$_2$, −70° C. to −20° C.

Efficacy of preferred aromatase inhibitors synthesized in accordance with examples:

The compounds synthesized above have been tested by the assay described by Thompson and Siiteri (J. Biol. Chem. 249, 5364–5372, 1974) slightly modified as set forth below, and have been found to be effective inhibitors of the activity of placental aromatase.

Microsomal aromatase was obtained from human placenta. A reaction vessel was prepared containing microsomes (0.124 mg protein/ml), NADPH (0.625 mM), [$^3$H]androstenedione (0.33 μM) and increasing concentrations of the potential inhibitor being tested in buffer (800 μl) (0.1M KH$_2$PO$_4$, pH 7.5). The conversion of androstenedione to estrone was allowed to proceed at 37° C. for 30 min and stopped by addition of 200 μl of charcoal suspension (25 mg/ml) in the same buffer. After centrifugation, tritiated water contained in 100 μl of supernatant was counted. The amount of tritiated water is proportional to the amount of transformed [$^3$H] androstenedione. Ki values were calculated by the Dixon method (Dixon, M., 1953, Biochem. J. 55, 170–171) and reported in Table 1 below:

TABLE I

| Potency of selected compounds as inhibitors of aromatase activity | |
|---|---|
| Compound | Ki (μM) |
| EM 173 | 0.2 |
| EM 176 | 0.9 |

TABLE I-continued

| Potency of selected compounds as inhibitors of aromatase activity | |
|---|---|
| Compound | Ki (μM) |
| EM 198 | 0.6 |

As shown in Table 1, each of EM 173, EM 176 and EM 198 showed aromatase inhibitory activity.

What is claimed is:

1. An aromatase-inhibiting compound represented by the following molecular structure:

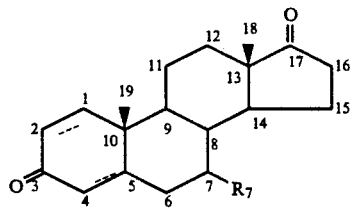

wherein the dotted line represents an optional double bond;
wherein R$_7$ is selected from the group consisting of alkenyl and alkynyl.

2. A pharmaceutical composition comprising a pharmaceutically acceptable diluent or carrier and therapeutical effective amount of the aromatase-inhibiting compound of claim 1.

3. The compound of claim 1 where the A/B ring junction of said molecular structure is in trans configuration.

4. A pharmaceutical composition comprising a pharmaceutically acceptable diluent or carrier and therapeutical effective amount of the aromatase-inhibiting compound of claim 3.

5. The compound of claim 1 wherein the AB-ring structure of said molecular structure is in cis configuration.

6. A pharmaceutical composition comprising a pharmaceutically acceptable diluent or carrier and therapeutical effective amount of the aromatase-inhibiting compound of claim 5.

7. The compound 7α-allyl 4-androsten-3,17-dione: "EM 173"

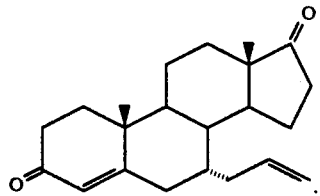

8. A pharmaceutical composition comprising a pharmaceutically acceptable diluent or carrier and therapeutical effective amount of the aromatase-inhibiting compound of claim 7.

9. The compound 7α-allyl-5β-androstan-3,17-dione: "EM 176"

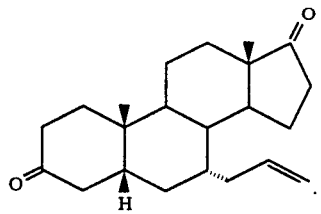

10. A pharmaceutical composition comprising a pharmaceutically acceptable diluent or carrier and therapeutical effective amount of the aromatase-inhibiting compound of claim 9.

11. The compound 7α-allyl-5α-androstan-3,17-dione: "EM 198"

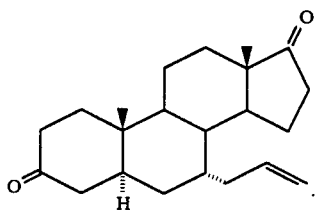

12. A pharmaceutical composition comprising a pharmaceutically acceptable diluent or carrier and therapeutical effective amount of the aromatase-inhibiting compound of claim 1.

13. The compound 7α-propyl-5α-androstan-3,17-dione: "EM 199"

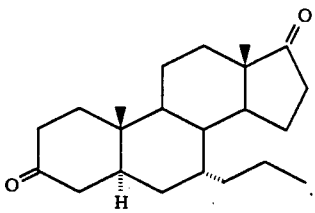

14. A pharmaceutical composition comprising a pharmaceutically acceptable diluent or carrier and therapeutical effective amount of the aromatase-inhibiting compound of claim 13.

15. The compound of claim 1 where all atoms of $R_7$ are separated from a ring carbon of the B ring of said compound by no more than seven intervening atoms.

16. A pharmaceutical composition comprising a pharmaceutically acceptable diluent or carrier and a therapeutically effective amount of the aromatase-inhibiting compound of claim 15.

17. The compound of claim 15 wherein $R_7$ includes at least two positions of unsaturation.

18. A pharmaceutical composition comprising a pharmaceutically acceptable diluent or carrier and therapeutical effective amount of the aromatase-inhibiting compound of claim 17.

19. The compound of claim 1 wherein $R_7$ is in the alpha position and is $-CH_2-Y$, wherein Y is selected from the group consisting of: $-CH=CH_2$, $-CH=CHCH_3$, $-C\equiv CH$, $-C\equiv-CH_3$.

20. A pharmaceutical composition comprising a pharmaceutically acceptable diluent or carrier and a therapeutically effective amount of the aromatase-inhibiting compound of claim 19.

21. An aromatase-inhibiting compound having the following molecular structure:

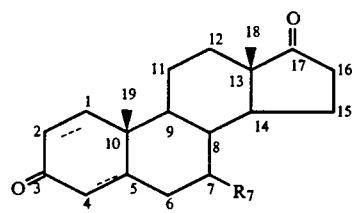

wherein B is methyl or ethyl;
wherein the dotted line represents an optional double bond; and
wherein $R_7$ is selected from the group consisting of alkenyl and alkynyl.

22. A pharmaceutical composition comprising a pharmaceutically acceptable diluent or carrier and therapeutical effective amount of the aromatase-inhibiting compound of claim 21.

23. A pharmaceutical composition comprising a pharmaceutically acceptable diluent or carrier and therapeutical effective amount of the aromatase-inhibiting compound of claim 21.

24. The compound 7α-(2-propynyl)-4-androsten-3,17-dione: "EM-235"

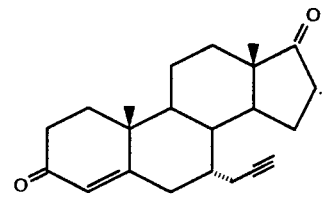

25. A pharmaceutical composition comprising a pharmaceutically acceptable diluent or carrier and therapeutical effective amount of the aromatase-inhibiting compound of claim 24.

26. The compound of claim 1, wherein $R_7$ is alkenyl.

27. The pharmaceutical composition of claim 2, wherein $R_7$ is alkenyl.

28. The compound of claim 1, wherein $R_7$ is $C_1$–$C_4$ alkenyl.

29. The pharmaceutical composition of claim 2, wherein $R_7$ is $C_1$–$C_4$ alkenyl.

30. The compound of claim 21, wherein $R_7$ is alkenyl.

31. The pharmaceutical composition of claim 22, wherein $R_7$ is alkenyl.

32. The compound of claim 21, wherein $R_7$ is $C_1$–$C_4$ alkenyl.

33. The pharmaceutical composition of claim 22, wherein $R_7$ is $C_1$–$C_4$ alkenyl.

34. The compound of claim 1, wherein $R_7$ is $C_1$–$C_4$ alkenyl or $C_1$–$C_4$ alkynyl.

35. A pharmaceutical composition comprising a pharmaceutically acceptable diluent or carrier and a therapeutically effective amount of the aromatase inhibiting compound of claim 34.

* * * * *

UNITED STATES PATENT AND TRADEMARK OFFICE
CERTIFICATE OF CORRECTION

PATENT NO. : 5,227,375
DATED : July 13, 1993
INVENTOR(S) : Fernand Labrie et al.

It is certified that error appears in the above-indentified patent and that said Letters Patent is hereby corrected as shown below:

Column 1, line 19, change "synthesis" to --synthesizes--;
    line 41, delete ")".
Column 3, line 36, change "—C≡CH$_3$," to -- —C≡C-CH$_3$ --;
    line 44, change "4andros-" to -- 4-andros- --;
    line 47, change "5α-androstanedione" to --5ß-androstanedione--.
Column 4, line 13, change "alkylene" to --alkenyl--; change "alkylnylene" to --alkynyl--;
    line 44, change "ß-allyl" to --α-allyl--.
Column 5, line 10, change "7α-allyl-16-oxo-5ß-3,17-dione" to -- 7α-allyl-16-oxo-5ß-androstan-3,17 dione --.
Column 6, line 38, change "SCHEMA" to --SCHEME--;
    line 39, change "SCHEMA" to --SCHEME--.

UNITED STATES PATENT AND TRADEMARK OFFICE
CERTIFICATE OF CORRECTION

PATENT NO. : 5,227,375
DATED : July 13, 1993
INVENTOR(S) : Fernand Labrie et al.

It is certified that error appears in the above-indentified patent and that said Letters Patent is hereby corrected as shown below:

Column 7, line 18, change "(3H,s,–$_{16}$C$\underline{H}_3$)." to
--(3H,s,–$_{18}$C$\underline{H}_3$).--;
line 24, change "The" (first occurrence) to
--Then--;
line 27, change "form" to --from--;
line 55, change "C$\underline{H}_2$" to --C$\underline{H}$=CH$_2$--;
line 57, after "CH–", insert --)--;
line 58, change "–$_{16}$C$\underline{H}_e$" to -- –$_{18}$C$\underline{H}_3$ --;
line 64, change "(3H,s,–$_{16}$C$\underline{H}_3$)." to --
(3H,s,–$_{18}$C$\underline{H}_3$).--.

Column 8, line 62, change "1H-NMR" to --$^1$H-NMR--;
change "-CH$_2$" to -- =CH$_2$--;
line 63, change "'CH=CH$_2$" to -- –CH=CH$_2$ --.

Column 10, line 6, change "chloroperbenzoicacid" to
--chloroperbenzoic acid--;
line 15, change "θ$_{max}$" to --$v_{max}$--.

Column 11, line 28, change "4androstan" to --4-androsten--.
Column 12, line 29, change "4androstan" to --4-androsten--.
Column 13, line 3, change "4androstan" to --4-androsten--.

UNITED STATES PATENT AND TRADEMARK OFFICE
CERTIFICATE OF CORRECTION

PATENT NO. : 5,227,375
DATED : July 13, 1993
INVENTOR(S) : Fernand Labrie et al.

It is certified that error appears in the above-indentified patent and that said Letters Patent is hereby corrected as shown below:

IN THE CLAIMS:

Claim 1, delete the molecular structure and insert:

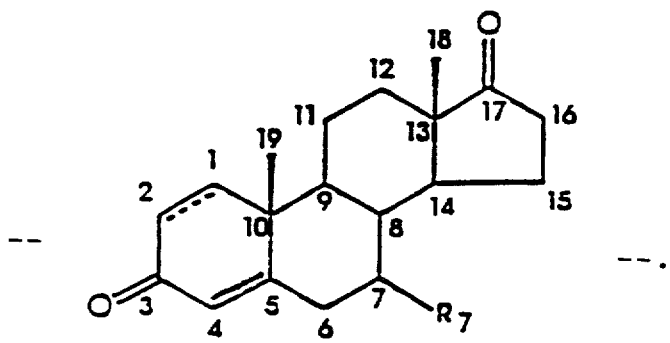

Delete claims 3-6 in their entirety.

Claim 7, line 1, change "7α-allyl 4-androsten" to --7α-allyl-4-androsten--.

Claim 12, line 4, change "1" to --11--.

Claim 19, line 4, change "—C≡—CH$_3$" to -- —C≡C—CH$_3$ --.

UNITED STATES PATENT AND TRADEMARK OFFICE
CERTIFICATE OF CORRECTION

PATENT NO. : 5,227,375
DATED : July 13, 1993
INVENTOR(S) : Fernand Labrie, et al Page 4 of 4

It is certified that error appears in the above-indentified patent and that said Letters Patent is hereby corrected as shown below:    Column 15, Claim 21, delete the molecular structure and insert:

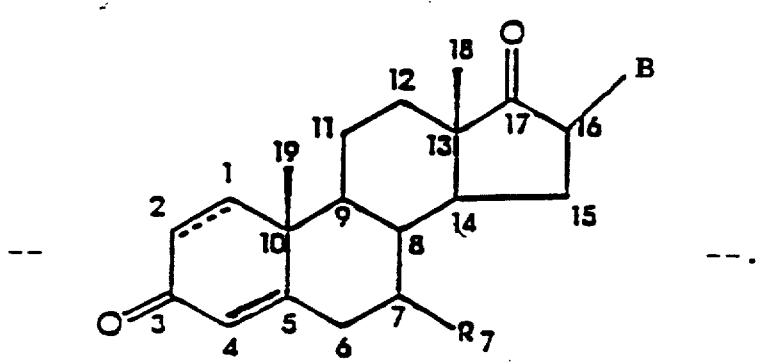

Column 16, claim 23, delete in its entirety.

Signed and Sealed this

Sixth Day of September, 1994

Attest:

BRUCE LEHMAN

Attesting Officer

Commissioner of Patents and Trademarks